United States Patent
Patrick et al.

[11] Patent Number: 5,868,933
[45] Date of Patent: *Feb. 9, 1999

[54] ANTIMICROBIAL FILTER CARTRIDGE

[76] Inventors: Gilbert Patrick, 635 Dixon School Rd., Kings Mountain, N.C. 28086; Arvind S. Patil, 1030 Southwent Dr., Davidson, N.C. 28036

[ * ] Notice: The term of this patent shall not extend beyond the expiration date of Pat. No. 5,762,797.

[21] Appl. No.: 877,080

[22] Filed: Jun. 17, 1997

Related U.S. Application Data

[63] Continuation-in-part of Ser. No. 573,067, Dec. 15, 1995, Pat. No. 5,762,797.

[51] Int. Cl.$^6$ .................................................. B01D 27/08
[52] U.S. Cl. ........................ 210/484; 210/488; 210/489; 210/493.1; 210/493.5; 210/494.1; 264/DIG. 48
[58] Field of Search ..................... 210/484, 488, 210/489, 493.1, 493.5, 494.1; 264/DIG. 48

[56] References Cited

U.S. PATENT DOCUMENTS

| | | | |
|---|---|---|---|
| 3,065,856 | 11/1962 | Goldman | 210/494 |
| 3,327,859 | 6/1967 | Pall et al. | 210/266 |
| 3,817,739 | 6/1974 | Abbott et al. | 71/67 |
| 3,828,934 | 8/1974 | Green et al. | 210/457 |
| 3,872,013 | 3/1975 | Nishino et al. | 210/317 |
| 3,998,740 | 12/1976 | Bost et al. | 210/195.1 |
| 4,032,688 | 6/1977 | Pall | 428/36 |
| 4,048,075 | 9/1977 | Colvin et al. | 210/484 |
| 4,102,785 | 7/1978 | Head et al. | 210/65 |
| 4,104,170 | 8/1978 | Nedza | 210/487 |
| 4,226,722 | 10/1980 | Jones | 210/287 |
| 4,642,192 | 2/1987 | Heskett | 210/628 |
| 4,660,779 | 4/1987 | Nemesi et al. | 242/7.02 |
| 4,769,096 | 9/1988 | Vander Giessen | 156/69 |
| 4,902,427 | 2/1990 | Szczepanik | 210/484 |
| 5,006,267 | 4/1991 | Vaughn et al. | 210/755 |
| 5,071,551 | 12/1991 | Muramatsu et al. | 210/266 |
| 5,269,919 | 12/1993 | von Medlin | 210/256 |
| 5,700,371 | 12/1997 | Koslow | 210/282 |
| 5,709,870 | 1/1998 | Yoshimura et al. | 424/404 |

FOREIGN PATENT DOCUMENTS

| 921835 | 2/1973 | Canada | 182/14 |
|---|---|---|---|

*Primary Examiner*—Ana Fortuna
*Attorney, Agent, or Firm*—Womble Carlyle Sandridge & Rice

[57] ABSTRACT

An antimicrobial filter cartridge having a perforated core member wrapped with a first microporous membrane, which is in turn overwrapped with second and third microporous membranes. The membranes are covered with a criss-cross wrapping of antimicrobial treated yarn. The filter cartridge is sized so as to fit tightly into a cartridge housing of a fluid filtration system. Fluid passing through the cartridge housing will be filtered by the filter cartridge to remove microorganisms from the water and which prevents the growth of bacterial and other microorganisms on the filter media.

28 Claims, 4 Drawing Sheets

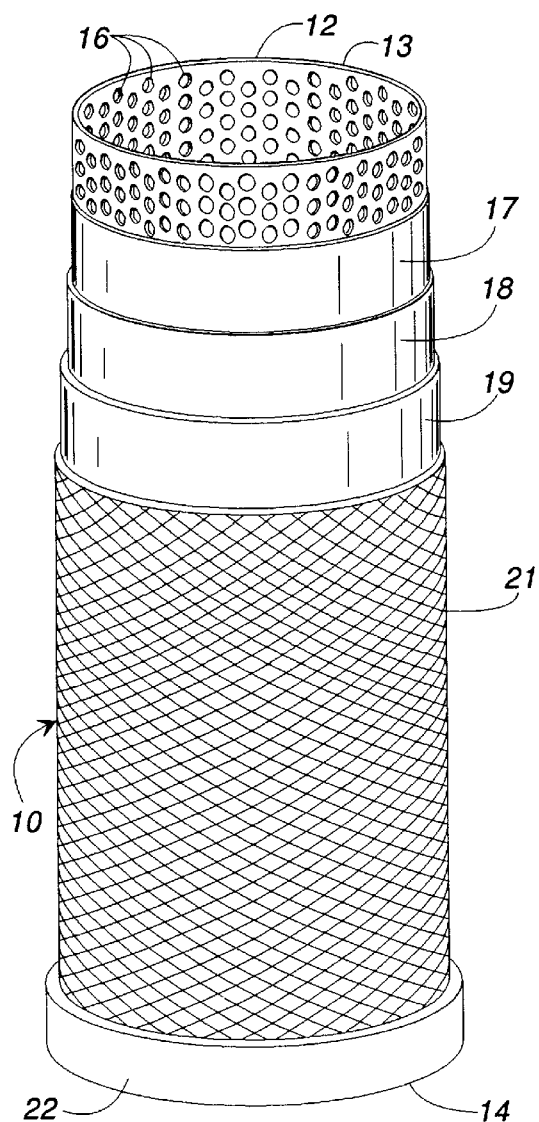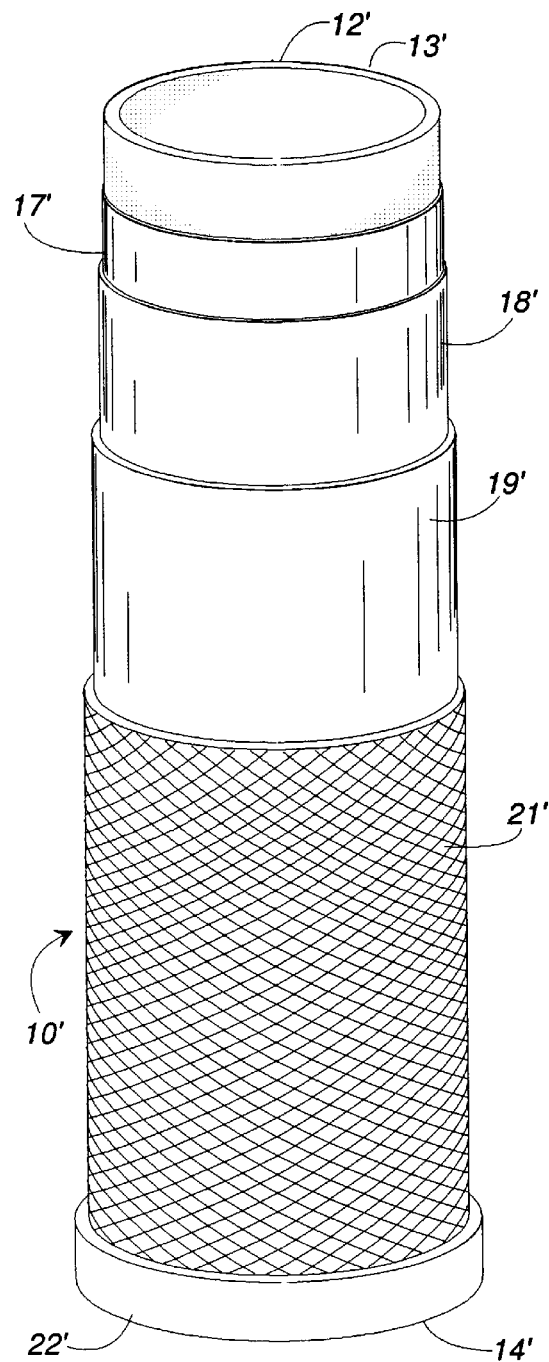
FIG. 1   FIG. 3

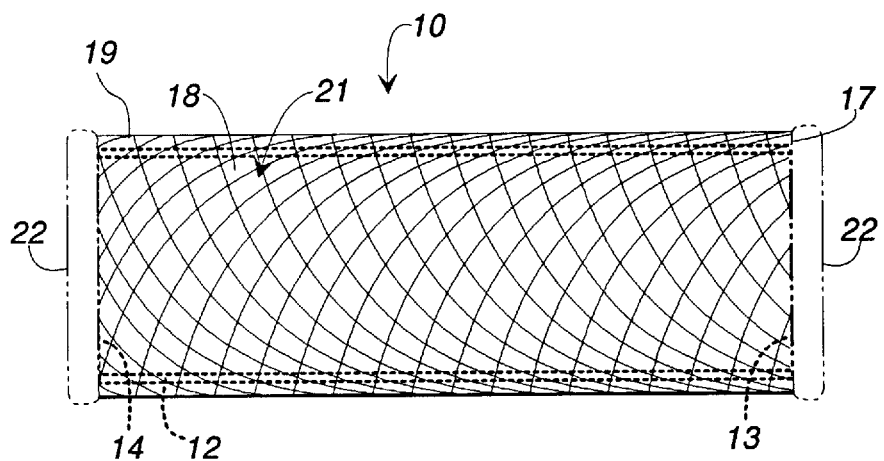
FIG. 2
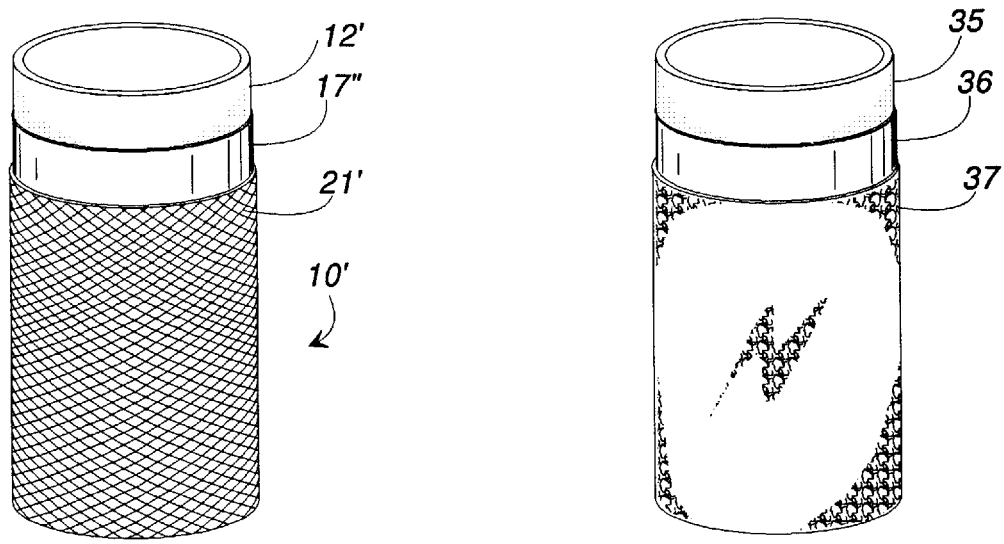
FIG. 4          FIG. 6

5,868,933

ANTIMICROBIAL FILTER CARTRIDGE

CROSS-REFERENCE TO RELATED APPLICATION

This application is a continuation-in-part of U.S. patent application Ser. No. 08/573,067, filed Dec. 15, 1995 U.S. Pat. No. 5,762,797.

FIELD OF THE INVENTION

This invention relates generally to filters for the purification of liquids. In particular, the present invention relates to an antimicrobial filter cartridge for a filtration system which is formed from layers of yarn and/or nonwoven webs or mats treated with an antimicrobial agent and wrapped about a core covered with a microporous membrane material to enable the filter cartridge to trap and remove low micron organic contaminant particles and to eliminate and inhibit growth of the bacterial and viral contaminants in the filtered flow to significantly reduce the level of particulate and bacterial contaminants within the water flowing through the filtration system.

BACKGROUND OF THE INVENTION

In recent years, the public has become increasingly aware of the deteriorating quality of our nation's and the world's water supply. Pollutants, biological and toxic waste and other contaminants are being introduced into water supplies at an ever increasing rate, making such water supplies unfit for drinking and other necessary uses. For example, medical patients with low immunity are now being requested not to drink tap water, and disease and illnesses linked to poor quality drinking water have increased dramatically in recent years. This problem is especially significant outside the United States where water quality has deteriorated to an all time low, with the major source of such contamination primarily being bacterial in nature. Many known solutions that currently exist to purify water, however, generally are too expensive or are not feasible in certain locations.

Of current filtration systems available, reverse osmosis systems are one of the most common solutions for improving water quality. Generally, these systems use a sediment removal filter in conjunction with activated carbon and a bacteriostatic membrane coated with oxides and halide of silver, as described in detail by Nishino in U.S. Pat. No. 3,872,013, placed between the filter and the water outlet. The membrane will prevent certain bacteria from leaving the filter and will retard their growth on the surface of the membrane, but will not check bacterial growth on the activated carbon or the ability of bacteria to multiply and produce toxins. Other mechanical filters such as ceramic filter cartridges that filter out bacteria of about 1 micron in size also are ineffective in retarding bacterial growth as the bacteria are collected on the surface of the filter.

Another type of biocidal reverse osmosis system is described in detail by Von Medlin in U.S. Pat. No. 5,269,919. Von Medlin further teaches the use of a polyiodide resin that releases iodide upon contact with bacteria and viral organisms to combat bacterial growth, and uses granular metal alloys and activated carbon to remove iodides released in the water. If not removed, these iodides would be harmful to human beings. In fact, EPA "Policy on Iodine Disinfection", initially developed in 1973 and reaffirmed in 1982, is that iodine disinfection is for short-term only, whenever iodine-containing species remain in the drinking water.

Thus, it appears that while a portion of the bacteria within the water supply will be caught by these filters, such trapped bacteria are allowed to grow within present water purification systems. Thus, the filters become a breeding ground for bacteria and toxins, possibly subjecting persons to potential harm by ingestion of toxic trace metals such as silver and copper halides, and other contaminants not filtered out of the water.

There has also been considerable development in wound or wrapped filters in which yarns are wrapped in varying patterns and layers about a perforated core. Increasing the number of layers and the tightness of the wrapping of the yarns generally has been found to be more effective at trapping particulate matter in the filter, but also suffers from the drawback of restricting the flow of water through the filter, thereby causing a pressure drop in water flow through the system. Typically, water pressure in a municipal water line in the United States runs between 60–80 psi. As conventional wound filters become more particulate laden, the pressure drop in the line caused by the restriction in water flow through the water filter increases upwards of 15–20 psi or greater. Such a pressure drop is an even greater problem overseas as line pressures generally are lower, on the order of 35 psi or less, so that the use of such filters cause the water flow to be so significantly restricted as to unduly limit the system.

In addition, activated carbon currently is used in many types of filters for removing odors, dissolved organics and unpleasant tastes from water supplies. A drawback to using activated carbon in filters is, however, that carbon is a source of nutrients for bacteria and once infected, carbon filters generally allow rapid multiplication of bacteria on the filters. As a result, carbon filters generally are required to have a warning to use only microbiological safe water for filtration through such filters. As a consequence, in many countries outside the U.S., where waters are not safe from microbiological contaminants, the use of such carbon filters can be dangerous and thus is generally not feasible. This has led to regulations banning the use of carbon in filters for certain uses and in certain areas.

It therefore can be seen that a need exists for an inexpensive and safe to use filter cartridge for a water filtration system that can filter microscopic organisms and prevent bacterial and viral growth within the filter media, without releasing life harming biocides that have to be further filtered out and which does not unduly restrict water flow through the system.

SUMMARY OF THE INVENTION

Briefly described, the present invention comprises a filter cartridge for a water filtration system for safely and effectively filtering microorganisms from drinking water and which substantially eliminates and prevents further growth of the bacteria and other microorganisms trapped by the filter. The filter cartridge includes an inner tubular-shaped perforated core of a metal, plastic or ceramic material. The core generally is covered with a series of microporous membranes having nominal pores of approximately 5.0 to 0.5 microns ($\mu$) and formed from a plastic material such as polyester, polypropylene, polysulfone or similar material. A first membrane layer is generally tightly wrapped around the core so that there are no spaces created between the membrane and the core, and preferably is slightly longer than the length of the core so as to overlap the two opposing ends of the core. Second and third membrane layers thereafter are wrapped about the core over the first membrane layer, with the second and third membrane layers generally being of the same type of microporous plastic or polyester material.

A yarn or nonwoven material that has been impregnated or otherwise treated with an antimicrobial agent typically is tightly wound about the membranes and core, over the third membrane, in a criss-cross or diamond-wrap pattern, creating approximately 1.0 $\mu$ diamond-shaped openings through which water can travel. It is also possible to wrap the microporous membrane with a nonwoven fibrous material mat or web containing antimicrobial treated fibers, thus replacing the yarn.

The filter cartridge also can include an extruded activated carbon core in place of the polypropylene core, with the activated carbon core having a nominal pore size of approximately 10.0 $\mu$. The carbon core generally will have been treated with an antimicrobial additive or agent such as is used to impregnate the yarn of the filter and/or the membrane layers. The activated carbon core is overlaid with at least one membrane layer and typically is overlaid with three or more separate membrane layers with each of the membrane layers having a pore size distribution between 5.0 to 0.5 $\mu$. Thereafter, an antimicrobial impregnated yarn is wrapped around the core and membrane, generally in a criss-cross or diamond-wrapped pattern thus creating diamond shaped openings through which water can travel.

The outer criss-cross wound section of the filter generally is made with sufficient thickness so that the filter cartridge can be tightly inserted into a cartridge housing, with minimal space between the filter cartridge and the housing walls. The ends of the membrane and yarn layers of the finished filter thereafter are sealed with an antimicrobial polymer or resin, forming end caps at the opposite ends of the filter. This insures that the fluids being treated will pass through the entire filter before exiting the system.

The filter cartridge is installed within a housing for a filtration system connected to a water supply. As water flows into the housing, the water flows down and through the filter cartridge, and exits the housing through an outlet port. The filter cartridge of the present invention removes microorganisms and other impurities from water flowing through the cartridge. Large impurities generally are removed by the criss-cross layers and/or by the microporous membranes. Microorganisms retained by the membranes are bacterial and viral contaminants that generally are forced into contact with the antimicrobial agent in the yarn and membranes and/or core due to the tight wrapping of the yarn and the membranes about the core. Thus, sufficient contact between the contaminants and the antimicrobial agent to remove and treat the contaminants is achieved without requiring long contact times between the fluid and the filter cartridge and without unduly restricting the water flow through the system.

It is, therefore, an object of the present invention to provide an antimicrobial filter cartridge that overcomes the above-discussed and other deficiencies of the prior art by providing a filter cartridge that substantially completely filters particulates and large microorganisms from water and prevents the growth of bacterial and viral contaminants within the filter media.

It is another object of the present invention to provide an antimicrobial filter cartridge that does not release harmful toxins into the water that must be removed from the water before the water can be safely consumed.

A further object of the present invention is to provide an antimicrobial filter cartridge that can be used in presently available filtration system housings including those used in reverse osmosis systems that will inhibit the growth of bacterial and viral contaminants and subsequent toxin production and will protect an activated carbon filter used in such a reverse osmosis filtering systems.

Still a further object of the present invention is to provide an antimicrobial filter cartridge that substantially collects and removes particulate and bacterial contaminants without creating a significant drop in pressure in the water flow.

Another object of the present invention is to provide an antimicrobial filter cartridge wherein nearly all of the water flowing into the filter cartridge comes into contact with an antimicrobial agent.

Another object of the present invention is to provide an antimicrobial filter having an activated carbon core impregnated with an antimicrobial agent.

Another object of the present invention is to provide an improved method of impregnating an activated carbon core for a filter system with an antimicrobial agent.

Other objects, features, and advantages of the present invention will become apparent to one with skill in the art upon examination of the drawings and the detailed description.

BRIEF DESCRIPTION OF THE DRAWINGS

FIG. 1 is a side elevational view of a preferred embodiment of the present invention, with portions cut away.

FIG. 2 is a side elevational view of the filter cartridge of the present invention with end caps installed.

FIG. 3 is a side elevational view of a second embodiment of the present invention having an activated carbon core, with portions cut away.

FIG. 4 is a side elevational view of the second embodiment of the present invention having an activated carbon core, with portions cut away.

FIG. 6 is a side elevational view of an additional embodiment of the present invention.

DETAILED DESCRIPTION

Figure 5:
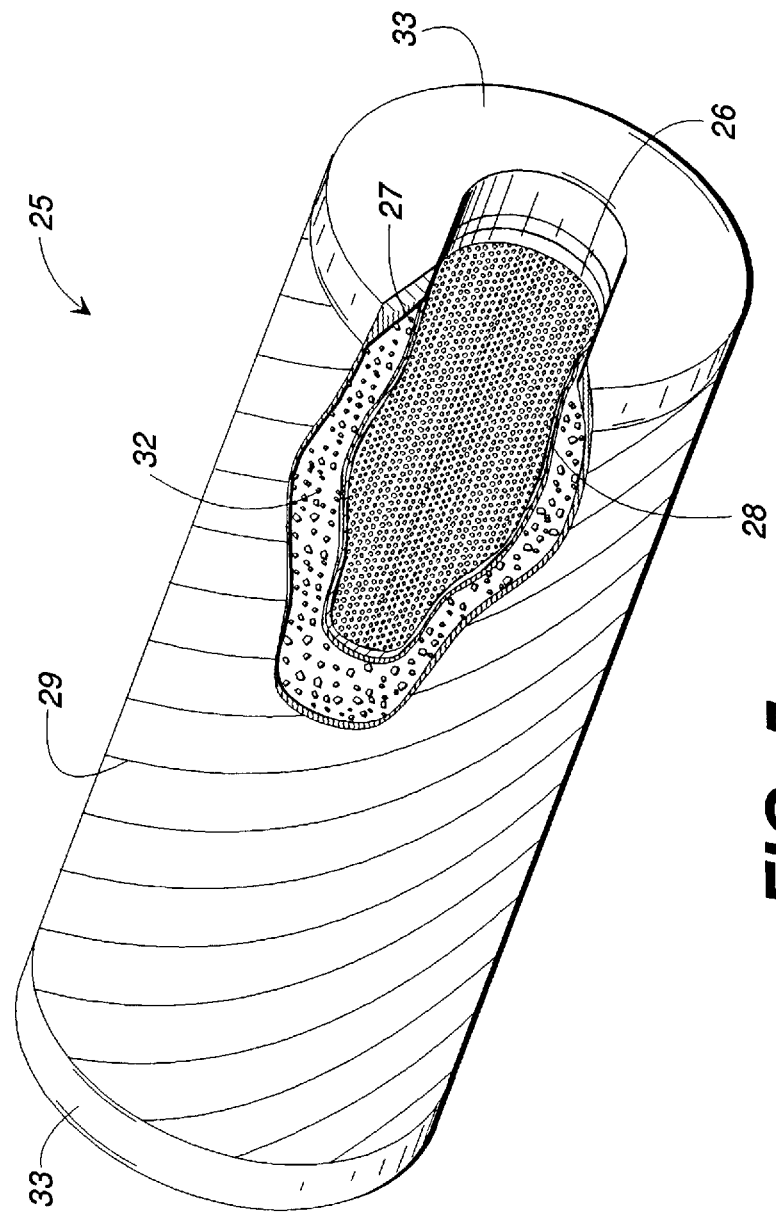
FIG. 5 is a perspective view, with portions broken away, of a further embodiment of the present invention.

Referring now to the drawings in which like numerals indicate like parts throughout the several views, FIG. 1 illustrates a preferred embodiment of a filter cartridge 10 constructed in accordance with the present invention. The filter cartridge 10 includes a hollow central perforated core 12 having open ends 13 and 14, and which can be formed from plastic, paper, metal, or can be a ceramic candle material, which is inherently perforated. The core is formed as a tube or cylinder approximately 5 to 30 inches in length and generally has a diameter of approximately 1 to 2 inches, although larger or smaller diameters can be used if necessary. A series of pores or perforations 16 at least approximately 10 microns ($\mu$) in size or larger generally are formed through the core at spaced positions along its length.

A first microporous membrane 17 is wrapped tightly around the core so as to cover it completely. Preferably, the membrane 17 is a thin film having a width slightly greater than the length of the core 12 so that the membrane overlaps each of the open ends 13 and 14 of the core by approximately 0.125 inches. The microporous membrane generally is formed from a material such as a polyester, polysulfone polymer, polyethylene, polypropylene or a similar porous plastic material, and can be treated with an antimicrobial agent. Preferably, the membrane will be a polysulfone polymer film having a nominal pore size of between approximately 5.0 $\mu$ to 0.5 $\mu$, such as a BTS-16, BTS-10 or BTS-5 membrane manufactured by MEMTEC America Corporation under the tradename Filtrite® typically having pores of 0.75 $\mu$ or greater, so that it will effectively keep most gram positive and gram negative bacteria and containment particles from flowing through the membrane into the interior of the perforated core.

A second microporous membrane layer 18 and a third microporous membrane layer 19 thereafter are wrapped about the core, overlying the first membrane layer 17 and the core. The second and third membrane layers typically are formed from the same polysulfone polymer membrane material as the first membrane layer i. e. a BTS-16, BTS-10 or BTS-5 membrane having pores of 0.75 $\mu$ or greater. The three layers effectively trap most bacteria and contaminant particles by reducing and limiting the path of the bacteria through the filter without significantly restricting water flow due to the larger size pores of the membranes.

A fibrous yarn 21 is wrapped in a close, tight winding over the microporous membranes 17–19, over the third membrane layer and extending along the length of the underlying perforated core. The yarn typically is between 10/1 c.c. to 0.3/1 c.c., preferably between 3/1 c.c. to 0.4/1 c.c., and is formed from spun fibers of white polypropylene, polyethylene, cellulose acetate, rayon, lyocell, acrylic, polyester, nylon or any other fibrous material that will support an antimicrobial agent. For some applications, the yarn further can be formed from nylon, cotton or a fibrillated filament yarn material, or combinations and blends of these polymers. The yarn is impregnated with an antimicrobial agent, which is preferably mixed with the yarn during spinning and formation of the fibers so that it is dispersed throughout the yarn fibers and will diffuse to the surface of the fibers during use of the filter cartridge.

The deniers of these fibers further can be between 0.3 dpf to 10 dpf, the preferable range based on cost and performance being 1.5 dpf to 6 dpf. These fibers typically are rendered antimicrobial, either by treating them topically or by impregnating them with the antimicrobial agent during their extrusion. The concentration of the antimicrobial agent in the fibers generally is between 100 to 10,000 ppm, preferably between 2000 ppm to 8000 ppm. The antimicrobial content of the final filter cartridge based on the yarn content should be between 2500 ppm to 10,000 ppm, preferably in the range of approximately 5000 ppm depending on the fibers used.

Preferably, the antimicrobial agent used to treat the yarn, and the microporous membranes if so desired, is practically insoluble in the water passing through and over the filter cartridge, and is safe, non-toxic, non-carcinogenic, non-sensitizing to human and animal skin and does not accumulate in the human body when ingested. Generally, therefore, the antimicrobial is a broad spectrum antimicrobial agent, i.e., it is equally effective against the majority of harmful bacteria encountered in water. For example, an antimicrobial agent such as 2,4,4'-trichloro-2'-hydroxydiphenol ether, or 5-chloro-2-phenol (2,4 dichlorophenoxy) commonly sold under the trademark MICROBAN®B, by Microban Products Co. typically will be used. However, it will be understood various other antimicrobial agents that are safe non-toxic and substantially insoluble in water can be used in the present invention.

The yarn 21 is wrapped in a criss-cross or diamond-patterned wrapping wound about the filter cartridge to form a criss-cross wrapping layer defining diamond-shaped openings or passages approximately 1.0 $\mu$ in size. The thickness of the criss-cross wrapping layer will determine the thickness of the filter cartridge. Preferably, the criss-cross wrapping layer is approximately ¼" thick, although the total thickness of the criss-cross wrapping layer 21 can be of greater or lesser thicknesses, depending on the size of the filtration system housing in which the filter cartridge is to be installed, so as to enable the filter cartridge to fit tightly into a housing of a filtration system. Once the filter has been wrapped to the desired, finished thickness, the yarn is cut and the end is tucked under or otherwise secured to a previous strand to prevent the yarn from unraveling.

As shown in FIG. 2, end caps 22 are applied over the open ends 13 and 14 of the core and the cartridge filter to seal the ends of the filter cartridge. The end caps 22 generally comprise a polyvinyl chloride (PVC) plastisol material containing an antimicrobial agent such as MICROBAN®B. The plastisol is poured in a liquid form into a shallow mold having an opened inside tube. A first end of the filter cartridge 10 is then set into the mold containing the plastisol liquid heated to a recommended temperature, for example 260° F., for approximately seven minutes or until the plastisol has sufficiently permeated and set in the yarn at the ends of the filter. The filter cartridge is removed and its opposite or second end is dipped into the plastisol liquid heated and set as above. The plastisol liquid is allowed to cool and solidify over the ends of the filter cartridge, whereupon the plastisol adheres to the fibrous yarn and to the protruding edges of the microporous membranes to seal the edges of the yarn and membranes at the ends of the filter cartridge, while still leaving the center of the cartridge open.

In an alternative embodiment, preformed end caps may be used in place of the end caps formed from the plastisol liquid to form the end caps. Such preformed caps generally are formed from a plastic material, such as polypropylene or similar material, treated with an antimicrobial agent. The caps are formed to ensure sealing of the ends of the microporous membrane and applied to the ends of the filter cartridge, preferably with an antimicrobial adhesive.

The end caps seal and cover the ends of the microporous membranes and criss-cross wrapping yarn layer of the filter cartridge at each end thereof. This forces the water or other fluid being filtered through the filtration system to pass through the sides of the filter cartridge to ensure that the water or other fluid will pass through and contact the antimicrobial yarn of the criss-cross wrapping layer about the filter and through the microporous membrane so that contaminants of at least 1.0 micron or larger are trapped and removed from the flow of water passing through the filter cartridge, and the bacteria and other microorganisms therein will be eliminated by contact with the antimicrobial surfaces of the yarn layer to substantially clean the water flow of bacteria and other contaminants.

In an additional embodiment shown in FIGS. 3 and 4, the perforated plastic core 12 (FIG. 1) is replaced with an extruded core of activated carbon 12' (FIGS. 2 and 3) treated with an antimicrobial agent. Activated carbon generally is used in water treatment for removal of offensive tastes, odor, chlorine, dissolved organic and removal of certain heavy metals in combination with special media. Activated carbon is, however, also a source of nutrients for heterotrophic bacteria, which tends to result in increased growth and bacterial activity, in the filter itself, causing the carbon to become fouled, resulting in a high pressure drop in the water flow and, at its worst, the multiplication and spreading of infectious bacteria. In the present invention, however, the activated carbon core 12' is formed having an antimicrobial agent impregnated therein, which kills and inhibits bacterial growth.

The antimicrobial treated activated carbon core 12' is formed by first homogeneously mixing an antimicrobial agent with a thermoplastic binder that melts and binds with carbon particles when heated in a homogeneous mixture. The antimicrobial agent preferably is the same antimicrobial material as used to treat the yarn at the filter, typically a 2,4,4'-trichloro-2'-hydroxy diphenol ether or 5-chloro-2-phenol (2,4-dichlorophenoxy) compound, that is commonly manufactured and sold under the trademark "MICROBAN®B" by Microban Products Company, Huntersville, N.C., or an equivalent antimicrobial agent that is insoluble in water. It is important that the antimicrobial agent not leech into the water being filtered during the filtration process and therefore by using the above-described antimicrobial agent or its equivalents, which are insoluble in water, such antimicrobial agents are safe to use in the water filtration process carried out by the present invention.

The binder with which the antimicrobial agent is mixed typically is a low density polyethylene powder or a similar binder material, such as polypropylene, polyester, fluropolymer, nylon or aramids, that easily and substantially completely melts and binds with carbon particles. Typically, the concentration of the MICROBAN®B antimicrobial agent applied with the binder will be in the range of approximately 50–10,000 ppm (parts per million) based upon the weight of the activated carbon being treated. Preferably, a concentration of 5,000 ppm of the MICROBAN®B antimicrobial agent is used based on the weight of the activated carbon. The antimicrobial treated binder is added to granular activated carbon, being uniformly mixed therewith. The entire mixture thereafter is heated to a temperature of approximately 250°–350° F. It will also be understood that when other polymeric binder materials are used, typically the mixtures are heated to temperatures above the melting points for each of these polymers. In general, the entire mixture is comprised of 5%–30% binder, typically 20% being the desired level, and the remaining portion comprising activated carbon granules. After the mixture has been heated to its melting point, the mixture is then extruded into a desired shape to form antimicrobial treated activated carbon core as shown in FIGS. 3 and 4.

Tests conducted on filter cartridges using antimicrobial treated activated carbon core of the present invention showed that there was virtually no detectable antimicrobial agent in the filtered water at a measured sensitivity of 50 parts per billion. Further, even after 72 hours of water standing in and about the filter cartridge, only 98 parts per billion of the antimicrobial agent was detected. Thus the antimicrobial compound appears to have been irreversibly absorbed by the carbon making use of the present invention treated with this antimicrobial material safe for use in filtering water, including drinking water.

As shown in FIGS. 3 and 4, the antimicrobial treated activated carbon core 12' of the additional embodiment of the present invention is wrapped with at least a first microporous membrane 17' such as a BTS-16, BTS-10, or BTS-5 polysulfone membrane having a pore diameter of approximately 0.75 $\mu$ or greater. Typically, second and third microporous membrane layers 18' and 19' (FIG. 3) are thereafter applied over the first microporous membrane layer 17' and carbon core 12', as illustrated in FIG. 3. It is also possible in some applications to use one microporous membrane layer 17" (FIG. 4), with the microporous membrane having pores of smaller diameter as illustrated in FIG. 4 for some applications. Thereafter, the microporous membranes and carbon core are wrapped with an antimicrobial treated yarn 21', which typically has been treated with an antimicrobial agent such as MICROBAN®B or similar material. The yarn generally is wrapped in a criss-cross or diamond wrapped pattern (FIGS. 3 and 4) and is applied in the sufficient thickness to provide the filter cartridge with sufficient thickness to fit snugly within a filter housing for a fluid filtration system. After the filter has been wrapped to a desired thickness, the yarn is cut and its ends secured, such as with end caps, to prevent the yarn from unraveling.

Additionally, if the water flow through the filter cartridge is to be reversed, flowing from inside of the cartridge out the sides thereof, the layering of the antimicrobial yarn/nonwoven material and the microporous membrane over the core is reversed. Thus, the core first is wrapped with the antimicrobial yarn/nonwoven mat, then overlaid with the microporous membrane. As a result, the water first will contact the antimicrobial yarn, to kill bacteria therein and thereafter contacts the microporous membrane, which traps and removes contaminant particles from the water flow. With such a construction, the filter cartridge of the present invention still provides a substantial cleaning of the water flow passing therethrough in the amount of contaminants and bacteria removed from the water flow.

FIG. 5 illustrates still a further embodiment of the filter cartridge 25 of the present invention. In this embodiment, the filter cartridge 25 includes a perforated inner tubular core 26 formed from plastic, paper, metal, compressed activated carbon or ceramic candles. At least one microporous membrane layer 27 is wrapped about the perforated inner core 26, with each microporous membrane generally being a thin film having a series of pores of approximately 0.75 $\mu$, such as a polysulfone membrane. An outer layer of an antimicrobial yarn 28 is wrapped about the core and membrane. The yarn typically is wrapped in a criss-cross type pattern or other desired pattern covering the microporous membrane (s). An outer shell 29 is received over the yarn layer, with the shell spaced from the yarn layer to form a void or space 31 therebetween. The shell typically is formed from a plastic such as polyethylene, polypropylene or PVC and is substantially porous, having pores of approximately 1 $\mu$–10 $\mu$ formed therein.

An activated carbon filling or bed 32, generally formed from granules of activated carbon treated with an antimicrobial agent as discussed above, is received within the void between the antimicrobial yarn and the outer shell forming a carbon bed between the shell and the core. As with the activated carbon core of the embodiment of FIGS. 3–4, the antimicrobial treated activated carbon bed kills bacteria within the water flow and prevents bacterial growth while removing odors, taste, etc. without releasing the antimicrobial agent into the filtered water. Thereafter, end caps 33 are applied over the ends of the filter cartridge to seal the void and the ends of the filter cartridge. With such construction, as the bacteria and particular contaminants are passed through the sides of the filter, the bacteria are contacted by and neutralized by the antimicrobial yarn and the carbon filling, as the contaminant particles also are filtered out of the water flow by the activated carbon filling in the microporous membrane. In addition, the filter cartridge also can be formed without the antimicrobial yarn, and with the antimicrobial treated, activated carbon filling applied between the membrane and the outer shell.

FIG. 6 shows still a further embodiment of the present invention, in which a core 35 either constructed of polypropylene or similar plastic material having a series of perforations and pores formed therein, or from activated charcoal impregnated with an antimicrobial agent, as discussed above, and is naturally porous, is overlaid with a microporous membrane 36. The membrane typically will be a plastic or polymer membrane such as a polysulfone polymer, generally having a pore size of approximately 0.35 $\mu$ or greater. The microporous membrane generally is wrapped about the core, with the ends of the microporous membrane overlapping the ends of the core so as to substantially seal and cover the core. A fiber mat 37 is wrapped about the membrane, with the fiber mat comprising a fibrous material formed from a plastic such as polypropylene, polyethylene, polyester, nylon, aramid fibers, rayon, acrylic, cellulose acetate or similar fibrous material treated with an antimicrobial chemical or agent such as MICROBAN®B. A fibrous mat is wrapped about the microporous membrane and core, with the ends of the fibrous mat being folded over and sealed over the ends of the microporous membrane and core such as with plastisol end caps. In addition, it is also possible to use additional microporous membranes to provide multiple layers of microporous membranes, with the multiple layers of microporous membranes generally having larger diameter pores in the order of approximately 0.75 $\mu$ or greater.

OPERATION

Figure 7:
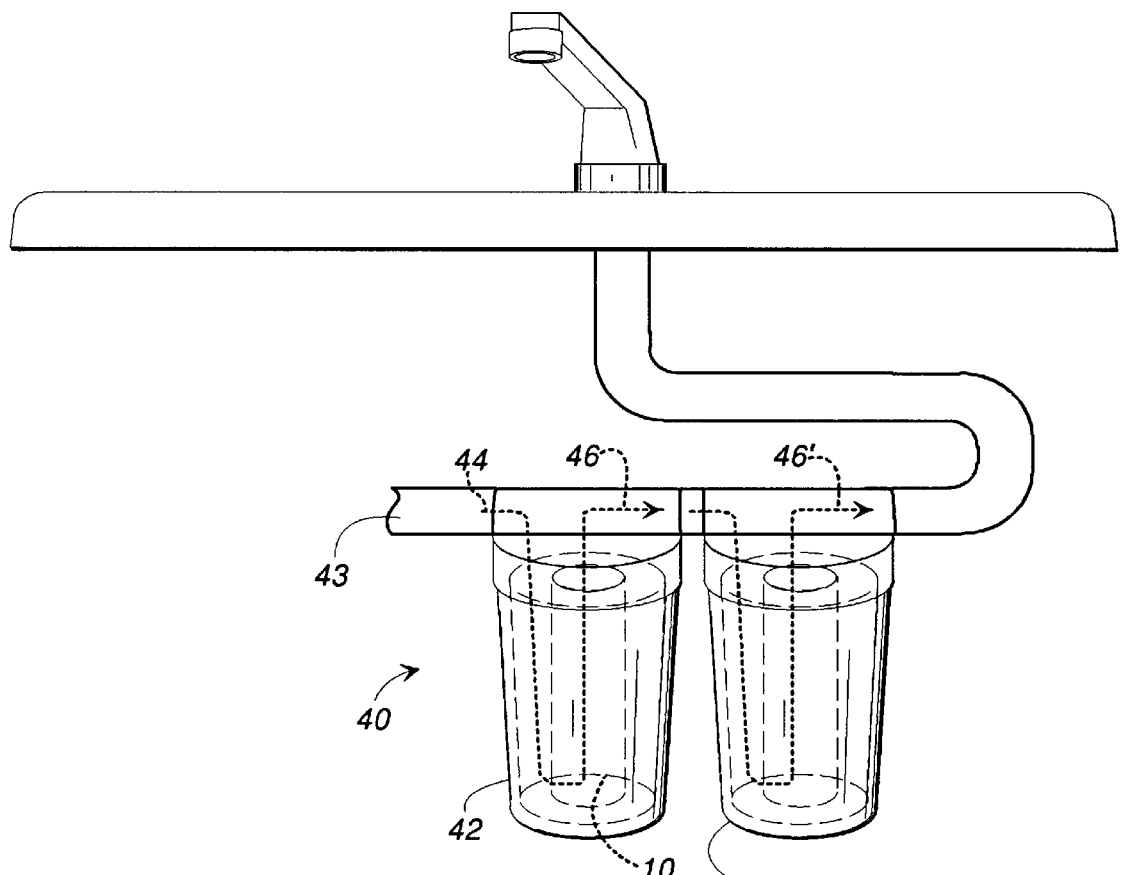
FIG. 7 is a schematic illustration of the filter cartridge of the present invention, showing the filter cartridge installed and used in an undersink filtration system.
Figure 8:
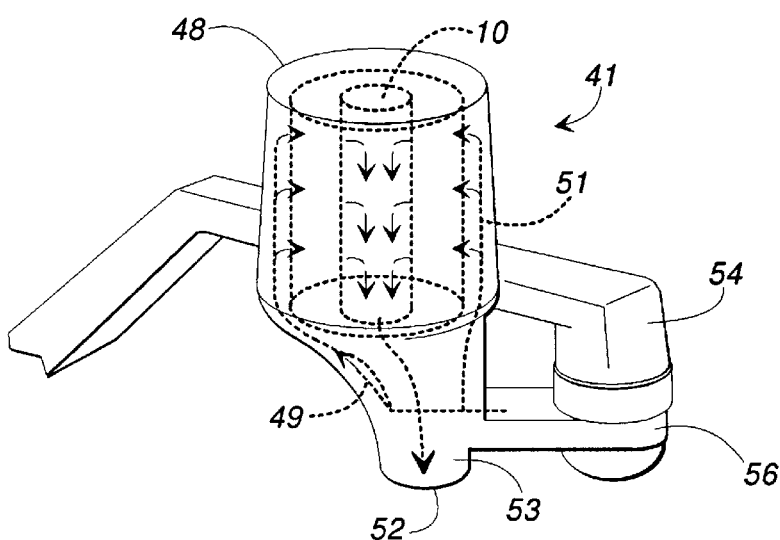
FIG. 8 is a schematic illustration of the filter cartridge of the present invention, showing the filter cartridge installed and used in a faucet filtration system.

In use, the filter cartridge 10 typically is mounted within the housing of a conventional water filtration system such as an undersink system 40 as shown in FIG. 7 or in a faucet mounted filtration system 41 as shown in FIG. 8. In the system of FIG. 7, the filter cartridge 10 is fitted snugly inside a filter cartridge housing 42 and the filtration system 40 is connected to a water source at the inlet end of the housing. The water is supplied to the filtration system at a desired flow rate and flows into the upstream or inlet end 43 of the housing as indicated by arrows 44. The water flows through the filter cartridge and out of the housing, whereupon the filter cartridge 10 traps and removes particulate contaminants and bacteria within the water flow to clean and purify the water flow before the water flow exits the housing through an outlet port 46. An additional filter cartridge housing 42' can be mounted downstream from the housing 42 for further cleaning of the water flow.

In the water filtration system of FIG. 8, the faucet mounted filtration system 41 includes a housing 48 having an inlet 9 and internal flow passages 51. An outlet port or spout 52 is formed at the base 53 of the housing 48 and communicates with the flow passage 51. The housing 48 is connected to a faucet 54 by a connecting portion 56 which fits over the outlet end of the faucet and which channels a flow of water therethrough and into the housing. As FIG. 8 illustrates, as the water flows into the filtration system from the faucet, it is directed along inlet flow passages, as indicated by arrows, through the filter and out through the outlet flow passage through the outlet port 52 with the water having been substantially cleaned and purified by the filter cartridge.

In the use of the filter cartridge 10 of the present invention in both of the filtration systems discussed above, the flow of water, as indicated in FIGS. 7 and 8 passes through the sides of the filter cartridge and out the open ends of the core. It will, however, be understood by those skilled in the art that the filter cartridge of the present invention functions equally well if the water flow were to be reversed so as to flow in through the ends of the cartridge and out through the sides of the cartridge, without affecting the ability of the cartridge to trap and retard bacteria within the flow. Under the alternate flow conditions the sequence of membrane and antimicrobial yarn may have to be altered.

Examples of the effectiveness of the present invention for cleaning and purifying a fluid flow are discussed below.

EXAMPLE #1

A test was conducted on a first filter sample constructed with a porous polypropylene core approximately 1/8" in diameter about which a BTS-30 type polysulfone polymer microporous membrane was wrapped, with the membrane having a nominal pore size of less than 0.35 $\mu$. A first spiral winding of polypropylene yarn impregnated with MICROBAN® antimicrobial agent was wrapped about the microporous membrane, followed by a 10 $\mu$ rated criss-cross winding of the same antimicrobial treated yarn. A second layer of the BTS-30 microporous membrane, having a pore size of less than 0.35 $\mu$, was wrapped over the criss-cross winding of yarn, followed by a second spiral winding of yarn and a second 10 $\mu$ criss-cross winding of antimicrobial impregnated polypropylene yarn. The ends of the filter cartridge were sealed with end caps of a PVC plastisol. This first filter sample was subjected to bacteriological testing in a repeated challenge test under municipal water line conditions.

In this test, coliform bacteria were introduced into the influent water in quantities of approximately 0.5 million colony forming units (CFUs). After approximately five minutes, the filtered effluent water flow was tested for the presence of the coliform bacteria. This process was repeated four times with additional quantities of 0.5 million CFUs of coliform bacteria being introduced into the influent water at varying intervals and with the effluent water thereafter being tested after a waiting period of approximately 5 minutes for bacterial contaminant levels and pressure drop between the influent and effluent flows.

| | Results | | |
|---|---|---|---|
| INJECTED SAMPLE AND TIME | FLOW (Tapwater) Gallons per Minute | PRESSURE DROP | TOTAL COLIFORM (Colonies per cc) |
| 13:25 inject 10 cc (.5 million CFU) | 1.99 | 16 | — |
| 13:30 | 1.95 | 15 | 0 |
| 13:35 inject 10 cc (.5 million CFU) | 1.99 | 16 | — |
| 13:40 | 1.95 | 16 | 0 |
| 13:42 inject 10 cc (.5 million CFU) | 1.95 | 16 | — |
| 13:47 | 2.07 | 17 | 0 |
| 13:48 inject 10 cc (.5 million CFU) | 2.03 | 17 | — |
| 13:53 | 2.03 | 17 | 0 |
| 13:54 inject 10 cc (.5 million CFU) | 2.03 | 17 | — |
| 13:59 | 2.07 | 18 | 0 |

At the start of the test, the influent flow water outside the filter also was measured and was found to have concentrations of 49,500 CFUs of coliform bacteria per cc, and at the end of the test, the influent water flow outside the filter was measured and was found to have concentrations of 60,200 CFUs of coliform bacteria per cc.

Thereafter, a test was conducted under substantially the same conditions and parameters on a second sample filter constructed according to the present invention, with the test running until a total of 10,000 gallons of water had passed through the filter. The filter was constructed according to the present invention with a porous polypropylene core about which was applied three wrapping layers of a wet laid DT-15 polyester microporous membranes manufactured by Veratec Corporation, each having a weight of 4.3 ounces per square yard, a thickness of 4.2 millimeters, a mean flow pore diameter of 11.2 $\mu$ and a smallest detected pore of 1.87 $\mu$. Each of the membrane layers was tightly overlaid and wrapped about the polypropylene core, with the third membrane layer wrapped with a 1.0 $\mu$ rated criss-cross winding of the polypropylene yarn impregnated with MICROBAN®B antimicrobial agent. The ends of the filter were sealed with polyvinyl chloride plastisol end caps. The filter was tested for bacteriological contamination present in the effluent water flow and for detection of pressure drop in the water flow between the influent water and effluent water flow.

Results

| INJECTED SAMPLE AND TIME | FLOW (Tapwater) Gallons per Minute | PRESSURE DROP (lb.) | TOTAL COLIFORM (Colonies per cc) |
| --- | --- | --- | --- |
| 2:45 inject 10 cc (.5 million CFU) | 2.0 | 4 | — |
| 2:50 | 2.0 | 4 | 0 |
| 2:55 inject 10 cc (.5 million CFU) | 2.0 | 4 | — |
| 3:00 | 2.0 | 4 | 0 |
| 3:05 inject 10 cc (.5 million CFU) | 2.0 | 4 | — |
| 3:10 | 2.0 | 4 | 0 |
| 3:15 inject 10 cc (.5 million CFU) | 2.0 | 4 | — |
| 3:20 | 2.0 | 4 | 0 |
| 3:25 inject 10 cc (.5 million CFU) | 2.0 | 4 | — |
| 3:30 | 2.0 | 4 | 0 |

The filter construction according to the present invention also was tested for viral rejection under the conditions of a flow rate of 0.5 gallons per minute and was found to reduce viral activity in the water flow between the influent water flow and effluent water flow. Measurements conducted on the influent water flow detected $5.75 \times 10^7$ plaque-forming units of viral contaminants per milliliter in the influent water flow, while measurements on the effluent water flow after passing through the above-described filter detected only $6.0 \times 10^5$ plague-forming units of viral contaminants per milliliter, providing a reduction of 98.96% in viral activity of the water flow passing through the filter as described above.

The results of the tests conducted on the filters of the first sample filter design and the second sample filter design of the present invention appear to show that both filters are able to provide a substantially complete elimination and/or reduction of material contaminants in the filtered water flow. However, the filter of the present invention was able to achieve this substantially complete elimination or reduction of bacterial contamination with only a limited drop in the pressure between the influent water flow and the effluent water flow.

EXAMPLE 2

Bacteriological tests were conducted on an untreated activated carbon core (sample no. 1) and on the activated carbon core of the present invention which was impregnated with the MICROBAN®B antimicrobial agent. Under the test, each of the samples was immersed in 100 cc. of spiked water containing 5,000 CFUs per cc of E. coli bacteria.

Results
Sample No. 1—untreated activated carbon core:

| Time Of Measurement | Core Weight (gms) | Colonies Per cc |
| --- | --- | --- |
| Background/Start | N/A | 6220 |
| 24 Hours | 23.6381 | 8380 |
| 48 Hours | 24,0788 | 9140 |
| 120 Hours | 22.5115 | 11,600 |

Sample No. 2—activated carbon core of the present invention treated with 5,000 ppm MICROBAN®B antimicrobial agent.

| Time Of Measurement | Core Weight (gms) | Colonies Per cc |
| --- | --- | --- |
| Background/Start | N/A | 5090 |
| 24 Hours | 28.7834 | 3810 |
| 48 Hours | 25.2915 | 4150 |
| 120 Hours | 26.1046 | 260 |

Thus, the results of these tests show that the untreated activated carbon core (sample 1) served as a source of nutrients for the e. coli bacteria, which tended to multiply and grow such that bacteriological activity increased significantly over the life of the test. In contrast, with the activated carbon core of the present invention (sample 2), which was treated with an antimicrobial agent, bacteriological activity significantly decreased over the life of the test.

In addition, a subsequent test was conducted on a filter cartridge constructed according to the present invention using the filter of sample 2 wrapped with a microporous membrane and a layer of polypropylene yarn impregnated with an antimicrobial chemical, and subjected to an influent water flow containing 2 ppm of chlorine at a flow rate of 0.75 gallons per minute. The results of this test showed a pressure drop between the influent and effluent water flow of approximately 1.5 psi and a reduction in the chlorine detected of 98.96%.

It will be apparent to those skilled in the art that while the present invention has been disclosed with references to preferred embodiments, many variations, modifications and additions can be made to the present invention without departing from the scope of the present invention as set forth in the following claims.

We claim:

1. An antimicrobial filter cartridge, comprising:
   an inner perforated core member;
   a first microporous membrane surrounding said core member;
   a second microporous membrane overlying said first membrane
   a third microporous membrane overlying said second membrane; and
   a layer of yarn wrapped around said membranes and said core.

2. The filter cartridge of claim 1, wherein said core member is selected from the group consisting of activated carbon, plastic, paper, metal and ceramic.

3. The antimicrobial filter cartridge of claim 1, wherein said microporous membranes have nominal pores of at least 0.75 $\mu$.

4. The filter cartridge of claim 1 and further including end caps applied to the filter cartridge at opposite ends thereof.

5. The antimicrobial filter cartridge of claim 1, wherein said yarn is made from a polymer selected from the group consisting of nylon, polypropylene, cellulose acetate, rayon, lyocell, acrylic, polyester, polyethylene, and mixtures thereof.

6. The antimicrobial filter cartridge of claim 1, wherein said membranes are made from a polymer material selected from the group consisting of polyester, polysulfone, polyethylene, and polypropylene.

7. An antimicrobial filter cartridge, comprising:
  an inner core member;
  a first microporous membrane surrounding said core member;
  a second microporous membrane overlying said first membrane,
  a third microporous membrane applied about said second membrane; and
  wherein said membranes are treated with an antimicrobial agent.

8. The antimicrobial filter cartridge of claim 7, wherein said yarn comprises a yarn impregnated with an antimicrobial agent selected from the group consisting of 2,4,4-trichloro-2hydroxy diphenol ether and 5-chloro-2phenol (2,4 dichlorophenoxy) compounds.

9. An antimicrobial filter cartridge, comprising:
  an inner tubular perforated core member having a first end and a second end;
  at least one microporous membrane surrounding said core member overlapping said first and second ends of said core member and having nominal pores of at least approximately 0.75 microns;
  an antimicrobial yarn wound about said membrane and said core member in a desired pattern and treated with an antimicrobial agent; and
  whereby as a fluid passes through the filter cartridge, the fluid contacts the antimicrobial yarn and microporous membrane which trap contaminant particles within the fluid and retard bacterial growth to clean the fluid of contaminants.

10. The filter cartridge of claim 9 and the antimicrobial filter cartridge of claim 1, wherein said antimicrobial yarn is made from a polymer selected from the group consisting of nylon, polypropylene, cellulose acetate, rayon, lyocell, acrylic, polyester, polyethylene, and mixtures thereof.

11. The filter cartridge of claim 9 and further including a second microporous membrane applied over said microporous membrane and a third microporous membrane applied over said second microporous membrane.

12. The filter cartridge of claim 9 and wherein said microporous membrane is treated with an antimicrobial agent selected from the group consisting of 2,4,4-trichloro-2 hydroxy diphenol and 5-chloro-2 phenol (2,4 dichlorophenoxy) compounds.

13. An antibacterial filter cartridge, comprising:
  a core formed from an activated carbon material treated with an antimicrobial agent;
  at least one microporous membrane layer wrapped about said core; and
  a layer of antimicrobial impregnated yarn wrapped about said core in a substantially criss-cross wound pattern.

14. The filter cartridge of claim 13 and wherein said antimicrobial treated activated carbon core is formed by applying an antimicrobial agent with a binder, mixing the binder with carbon particles, heating the binder and carbon particle mixture and extruding said carbon core.

15. The filter cartridge of claim 14 and wherein said antimicrobial agent is selected from the group consisting of 2,4,4'-trichloro-2-hydroxy diphenol ether and 5-chloro-2 phenol (2,4 dichlorophenoxy) compounds.

16. The filter cartridge of claim 13 and further comprising a second microporous membrane layer applied over said first microporous membrane layer and a third microporous membrane layer applied over said second microporous membrane layer.

17. The filter cartridge of claim 16 and the antimicrobial filter cartridge of claim 1, wherein said microporous membranes have nominal pores of at least 0.75 $\mu$.

18. The filter cartridge of claim 16 and wherein said membrane layers are treated with an antimicrobial agent.

19. An antimicrobial filter cartridge, comprising:
  an inner perforated core;
  at least one microporous membrane wrapped about said core;
  a fibrous web wrapped about said microporous membrane, surrounding said core, and impregnated with an antimicrobial; and
  whereby as a fluid flows through said fibrous web and core of the filter cartridge, contaminants and bacteria within the fluid are trapped and removed therefrom to substantially clean the fluid.

20. A bactericidal filter cartridge, comprising:
  a core formed from an activated carbon material treated with an antimicrobial agent;
  at least one microporous membrane applied to said core;
  a layer of antimicrobial yarn wound about said membrane and core in a substantially criss-cross winding having pores formed therethrough; and
  end caps applied at opposite ends of said core.

21. The bactericidal filter cartridge of claim 20 and further comprising a second microporous membrane layer applied over said first microporous membrane layer and a third microporous membrane layer applied over said second microporous membrane layer.

22. The bactericidal filter cartridge of claim 20 and wherein said microporous membranes are treated with an antimicrobial agent.

23. The bactericidal filter cartridge of claim 20 and wherein said microporous membranes include nominal pores of at least approximately 0.75 microns.

24. The bactericidal filter cartridge of claim 20 and wherein the antimicrobial yarn comprises a fibrillated filament yarn is impregnated with an antimicrobial agent in a concentration of approximately 50 to 10,000 ppm.

25. A method of forming an antimicrobial filter cartridge for a water filtration system, comprising the steps of:
  applying an antimicrobial agent to a binder;
  mixing the antimicrobial treated binder with carbon particles;

heating and extruding the carbon particle and antimicrobial treated mixture to form a carbon core member; and covering the core member with a yarn in a desired pattern.

26. A method of forming an antimicrobial filter cartridge for a water filtration system, comprising the steps of:

applying an antimicrobial agent to a binder:

mixing the antimicrobial treated binder with carbon particles, extruding the carbon particle and antimicrobial treated binder mixture to form a core member;

applying a first microporous membrane about the core member; and covering the core member with a yarn in a desired pattern.

27. The method of claim 26 and further including the step of applying second and third microporous membranes about the core member.

28. The method of claim 26 wherein the yarn is treated with an antimicrobial agent.

\* \* \* \* \*